United States Patent
Chen et al.

(10) Patent No.: US 10,030,262 B2
(45) Date of Patent: Jul. 24, 2018

(54) METHOD OF PERFORMING DIGITAL PCR

(71) Applicant: LIFE TECHNOLOGIES CORPORATION, Carlsbad, CA (US)

(72) Inventors: Caifu Chen, Palo Alto, CA (US); Casey McFarland, San Francisco, CA (US); David Keys, Alameda, CA (US)

(73) Assignee: Life Technologies Corporation, Carlsbad, CA (US)

(*) Notice: Subject to any disclaimer, the term of this patent is extended or adjusted under 35 U.S.C. 154(b) by 330 days.

(21) Appl. No.: 14/395,456

(22) PCT Filed: Apr. 19, 2013

(86) PCT No.: PCT/US2013/037352
§ 371 (c)(1),
(2) Date: Oct. 17, 2014

(87) PCT Pub. No.: WO2013/158982
PCT Pub. Date: Oct. 24, 2013

(65) Prior Publication Data
US 2015/0099644 A1     Apr. 9, 2015

Related U.S. Application Data (63) Continuation of application No. PCT/US2013/032598, filed on Mar. 15, 2013.

(60) Provisional application No. 61/635,584, filed on Apr. 19, 2012.

(51) Int. Cl.
| | | |
|---|---|---|
| *C12P 19/34* | (2006.01) | |
| *C12Q 1/686* | (2018.01) | |
| *C12Q 1/6851* | (2018.01) | |
| *C12Q 1/6858* | (2018.01) | |

(52) U.S. Cl.
CPC ........... *C12Q 1/686* (2013.01); *C12Q 1/6851* (2013.01); *C12Q 1/6858* (2013.01)

(58) Field of Classification Search
CPC ........ C12Q 2563/159; C12Q 2565/607; C12Q 1/6851; C12Q 1/6858; C12Q 2527/119; C12Q 2565/301; C12Q 1/686
USPC .................................................. 435/6.1, 91.2
See application file for complete search history.

(56) References Cited

U.S. PATENT DOCUMENTS

| | | |
|---|---|---|
| 2003/0003609 A1 | 1/2003 | Sauer et al. |
| 2005/0112631 A1 | 5/2005 | Piepenburg et al. |
| 2008/0166727 A1 | 7/2008 | Esfandyarpour et al. |
| 2009/0053719 A1* | 2/2009 | Lo ....................... C12Q 1/6851 435/6.11 |
| 2009/0127589 A1 | 5/2009 | Rothberg |
| 2009/0171078 A1 | 7/2009 | Lao et al. |
| 2009/0286286 A1 | 11/2009 | Lim |
| 2010/0311127 A1 | 12/2010 | Piepenburg et al. |
| 2014/0228245 A1 | 8/2014 | Hoffmann et al. |

FOREIGN PATENT DOCUMENTS

| | | |
|---|---|---|
| CN | 101743319 | 6/2010 |
| WO | 2005/118853 A2 | 12/2005 |
| WO | 2007/107710 | 9/2007 |
| WO | 2008/107014 | 9/2008 |
| WO | 2011/106368 | 9/2011 |
| WO | 2011/106629 | 9/2011 |
| WO | 2012/036679 | 3/2012 |
| WO | 2012/083189 A2 | 6/2012 |
| WO | 2013/045700 | 4/2013 |

OTHER PUBLICATIONS

Lun et al., Clinical Chemistry, vol. 54: No. 10, pp. 1664-1672, 2008.*
Vogelstein et al., PNA, vol. 96, pp. 9236-9241, 1999.*
Bentley, D. et al., "Accurate whole human genome sequencing using reversible terminator chemistry", Nature, vol. 456(6), (7218), 2008, 53-59.
Pemov, A. et al., "DNA analysis with multiplex microarray-enhanced PCR", Nucleic Acids Research, vol. 33, No. 2, 2005, 1-9.
SG11201406717R, Written Opinion dated Nov. 24, 2015, 8 pgs.
Glenn, Travis C., "Field Guide to Next-generation DNA Sequencers", Molecular Ecology Resources, vol. 11, No. 5, 2011, 759-769.
Morrison, et al., "Nanoliter High Throughput Quantitative PCR", Nucleic Acids Research, vol. 34, No. 18, e123, 2006, 1-9.
PCT/US2013/032598, International Preliminary Report on Patentability and Written Opinion dated Oct. 21, 2014, 6 Pages.
PCT/US2013/032598, International Preliminary Report on Patentability dated Oct. 30, 2014, 7 pages.
PCT/US2013/032598, International Search Report and Written Opinion dated Jun. 11, 2013.
PCT/US2013/037352, International Preliminary Report on Patentability and Written Opinion dated Oct. 21, 2014, 6 Pages.
Vogelstein, et al., "Digital PCR", Proc. Natl. Acad. Sci. USA, vol. 96, Aug. 1999, 9236-9241.
European Appl. No. 16177421.1, European Search Report dated Oct. 17, 2016, 1-7.
Singapore Appl. No. 11201406717R, IPOS Written Opinion dated Oct. 18, 2016, 1-10.

* cited by examiner

*Primary Examiner* — Cynthia B Wilder (57) ABSTRACT

A method of detection of a target nucleic acid is provided. The method includes fractionating a sample into a plurality of sample volumes wherein more than 50% of the fractions contain no more than 1 target nucleic acid molecule per sample volumes, and subjecting the plurality of sample volumes to conditions for amplification. The method further includes detecting a change in ion concentration in a sample volume wherein a target nucleic acid is present, counting the number of fractions with an amplified target nucleic acid, and determining the quantity of target nucleic acid in the sample.

20 Claims, 6 Drawing Sheets

METHOD OF PERFORMING DIGITAL PCR

BACKGROUND

Digital PCR (dPCR) is a refinement of conventional polymerase chain reaction (PCR) methods which can be used to directly quantify and clonally amplify nucleic acids (including DNA, cDNA, methylated DNA, or RNA). One difference between dPCR and traditional PCR lays in the method of measuring nucleic acids amounts. Both PCR and dPCR carry out one reaction per single sample, dPCR also carries out a single reaction within a sample, however the sample is separated into a large number of partitions and the reaction is carried out in each partition individually. This separation allows for sensitive measurement of nucleic acid amounts. DPCR has been demonstrated as useful for studying variations in gene sequences, such as copy number variation or point mutations.

In dPCR, a sample is partitioned so that individual nucleic acid molecules within the sample are localized and concentrated within many separate regions. The sample is fractionated by the simple process of dilution so that each fraction contains approximately one copy of DNA template or less. By isolating individual DNA templates this process effectively enriches DNA molecules that were present at very low levels in the original sample. The partitioning of the sample facilitates counting of molecules using Poisson statistics. As a result, each partition will contain "0" or "1" molecule(s), or a negative or positive reaction, respectively. While the starting copy number of a molecule is proportional to the number of amplification cycles in conventional PCR, dPCR is not dependent on the number of amplification cycles to determine the initial sample amount.

Current methods of dPCR analysis utilize fluorescent probes and light based detection methods to identify the products of amplification. Such approaches require sufficient amplification of the target molecules to generate enough signal to be detectable but can lead to additional error or bias. It is therefore desirable to provide an improved method for detection of nucleic acids of interest within a sample using alternate methods of analysis having increased accuracy and precision and which has a sensitivity that can be used in connection with dPCR-based approaches.

SUMMARY

Provided herein is a method of detection of a target nucleic acid comprising: fractionating a sample into a plurality of sample volumes wherein more than 50% of the fractions contain no more than 1 target nucleic acid molecule per sample volumes; subjecting the plurality of sample volumes to conditions for amplification; detecting a change in ion concentration in a sample volume wherein a target nucleic acid is present; counting the number of fractions with an amplified target nucleic acid; and determining the quantity of target nucleic acid in the sample. In some embodiments, the method further comprises combining a sample with primers and probes for amplification. The change in ion concentration may be an increase in ion concentration or may be a decrease in ion concentration. In some embodiments, the method may further include combining a sample with bead. In some embodiments, the method may include loading the sample on a substrate wherein the substrate includes at least one well. The substrate may be a glass, metal, metal oxide, silicon, ceramic, polymer coating or any combination thereof. The well may or may not be sealed with a sealing layer which may be solid or liquid such as, a cover slip, glass, plastic, composite material, optically transparent material, an immiscible fluid, or any other suitable sealing structure. Additionally, the surface of the well may be a treated surface. The treated surface may include a surface treatment to facilitate binding of a target molecule of interest including coating the surface with a hydrophilic coating, antibodies, streptavidin, avidin, thin-film coatings, nanofibers, oligonucleotides, any combination thereof or any other suitable surface treatment. Alternatively, the sample may be loaded onto a matrix, such as an extracellular matrix, a polymer matrix, or a gel, such as a polyacrylamide gel, agarose gel, or a hydrogel. The method may further include positioning each of the plurality of samples in a plurality of isolated positions, wherein each of the plurality of isolated positions is in chemical communication with a single sensor or wherein each of the plurality of isolated positions is in chemical communication with their own individual sensor. In some embodiments of the method, the change in ion concentration is an increase in ion concentration or a decrease in ion concentration. In some embodiments, the ion may be a positive ion such as a hydrogen ion or may be a negative ion such as a pyrophosphate molecule. The change in ion concentration may be indicated by a change in pH or may be converted to an electrical signal. In some embodiments, the method may include quantifying the amount of a target nucleic acid in a starting sample.

Further provided herein is a method for performing absolute quantification of a nucleic acid comprising: diluting a sample containing an initial amount of a target nucleic acid into a plurality of sample volumes wherein the percentage of reaction areas containing one or more target nucleic acid molecules is greater than 50% and less than 100%; subjecting the plurality of sample volumes to at least one amplification cycle; detecting a change in ion concentration in at least one of the plurality of sample volumes as a result of the at least one amplification cycle; and quantitating an initial amount of target nucleic acid. The change in ion concentration may be an increase in ion concentration, a decrease in ion concentration, a change in pH, may involve the detection of a positive ion such as a hydrogen ion, a negative ion such as a pyrophosphate molecule, or both positive and negative ion.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
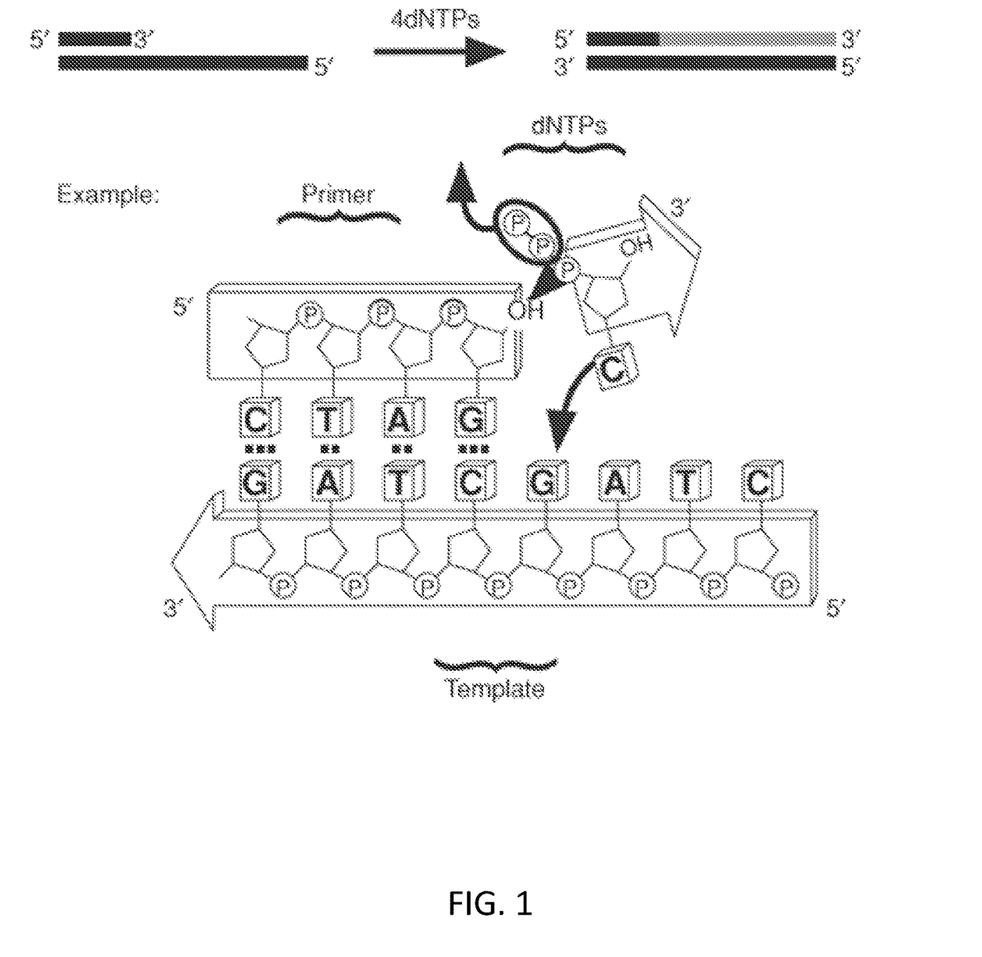
FIG. 1 shows an example of the extension phase of PCR.

Polymerase chain reaction (PCR) relies on thermal cycling, which consists of cycles of repeated heating and cooling of the reaction for DNA melting and enzymatic replication of DNA. The vast majority of PCR methods use thermal cycling, i.e., alternately heating and cooling the PCR sample to a defined series of temperature steps. These thermal cycling steps are necessary first to physically separate the two strands in a DNA double helix at a high temperature in a process called DNA melting. At a lower temperature, each strand is then used as the template in DNA synthesis by the DNA polymerase to selectively amplify the target DNA during the annealing phase and extension phases. Polymerases include heat-stable DNA polymerase such as, for example, Taq polymerase. The selectivity of PCR results from the use of primers that are complementary to the DNA region targeted for amplification under specific thermal cycling conditions. Primers (short DNA fragments) containing sequences complementary to the target region along with a DNA polymerase, are key components to enable selective and repeated amplification. FIG. 1 illustrates the extension of a complementary strand of DNA. During DNA replication as the deoxyribose-phosphate backbone is lengthened, a pyrophosphate molecule is liberated to drive the reaction forward. Additionally, the reaction also releases a single hydrogen ion, $H^+$, from the hydroxide group on the complimentary strand. In the methods provided herein, detecting a change in chemical concentration may indicate that amplification is occurring, and therefore, that the template DNA of interest is present in the reaction vessel.

Provided herein is a method of detection of a target nucleic acid comprising: fractionating a sample into a plurality of sample volumes wherein more than 50% of the fractions contain no more than 1 target nucleic acid molecule per sample volumes; subjecting the plurality of sample volumes to conditions for amplification; detecting a change in ion concentration in a sample volume wherein a target nucleic acid is present; counting the number of fractions with an amplified target nucleic acid; and determining the quantity of target nucleic acid in the sample. In some embodiments, the method further comprises combining a sample with primers and probes for amplification. The change in ion concentration may be an increase in ion concentration or may be a decrease in ion concentration. In some embodiments, the method may further include combining a sample with bead. In some embodiments, the method may include loading the sample on a substrate wherein the substrate includes at least one well. The substrate may be a glass, metal, metal oxide, silicon, ceramic, polymer coating or any combination thereof. The well may or may not be sealed with a sealing layer which may be solid or liquid such as, a cover slip, glass, plastic, composite material, optically transparent material, an immiscible fluid, or any other suitable sealing structure. Additionally, the surface of the well may be a treated surface. The treated surface may include a surface treatment to facilitate binding of a target molecule of interest including coating the surface with a hydrophilic coating, antibodies, streptavidin, avidin, thin-film coatings, nanofibers, oligonucleotides, any combination thereof or any other suitable surface treatment. Alternatively, the sample may be loaded onto a matrix, such as an extracellular matrix, a polymer matrix, or a gel, such as a polyacrylamide gel, agarose gel, or a hydrogel. The method may further include positioning each of the plurality of samples in a plurality of isolated positions, wherein each of the plurality of isolated positions is in chemical communication with a single sensor or wherein each of the plurality of isolated positions is in chemical communication with their own individual sensor. In some embodiments of the method, the change in ion concentration is an increase in ion concentration or a decrease in ion concentration. In some embodiments, the ion may be a positive ion such as a hydrogen ion or may be a negative ion such as a pyrophosphate molecule. The change in ion concentration may be indicated by a change in pH or may be converted to an electrical signal. In some embodiments, the method may include quantifying the amount of a target nucleic acid in a starting sample.

Further provided herein is a method for performing absolute quantification of a nucleic acid comprising: diluting a sample containing an initial amount of a target nucleic acid into a plurality of sample volumes wherein the percentage of reaction areas containing one or more target nucleic acid molecules is greater than 50% and less than 100%; subjecting the plurality of sample volumes to at least one amplification cycle; detecting a change in ion concentration in at least one of the plurality of sample volumes as a result of the at least one amplification cycle; and quantitating an initial amount of target nucleic acid. The change in ion concentration may be an increase in ion concentration, a decrease in ion concentration, a change in pH, may involve the detection of a positive ion such as a hydrogen ion, a negative ion such as a pyrophosphate molecule, or both positive and negative ion.

Figure 2:
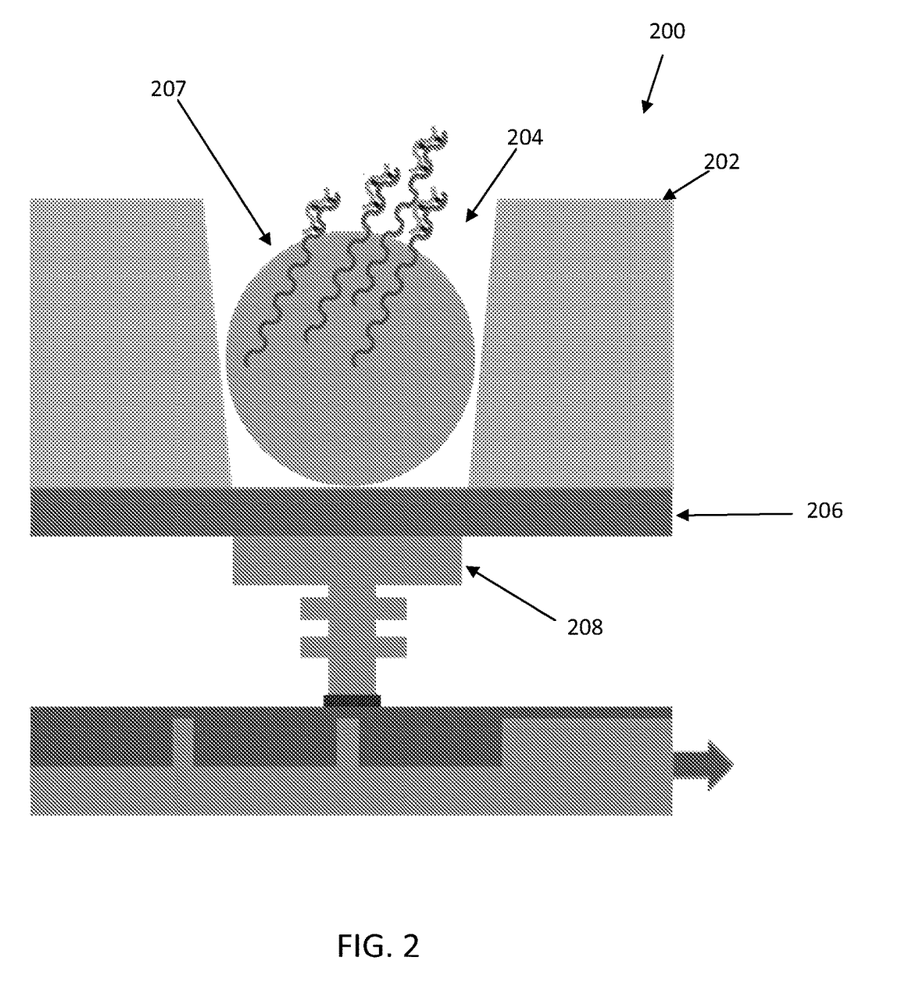
FIG. 2 shows one embodiment of a device for use with the method described herein.

FIG. 2A shows one embodiment of a device in which a single molecule of a target nucleic acid may be detected. As shown in FIG. 2A, a representative device 200 may include an etched substrate 202 including at least one well 204, which well 204 may be configured to contain and confine a volume of sample. An ion sensitive layer 206 may be in chemical communication with the well 204 and is in electrical communication with a sensor 208. In some embodiments, the well 204, or wells in an embodiment where there is more than one well, is in chemical communication with a single sensor, or each well 204 may be in chemical communication with its own individual sensor, as shown in FIG. 2A. In some embodiments the sensor may be a chemical field-effect transistor (chemFET) sensor, an ion-sensitive field effect transistor (ISFET), or any other suitable biosensor. In some embodiments, the sensor detects changes to ion concentration, pH, heat, enzyme activity, or any other form of energy emitted in response to a reaction occurring in the well. In some embodiments, the sensor can be configured to detect the release of a single hydrogen ion during a reaction. For example, as the template strand is being replicated, with each nucleotide binding occurrence the system may detect a change in ion concentration and report such change as a spike. In some embodiments, a bead 207 may be used to bind the DNA strands, as shown in FIG. 2A. Other embodiments of a suitable device are described in further detail in published U.S. Patent Publication No. 2010/0301398, which publication is incorporated by reference in its entirety.

During use, as amplification occurs and as incorporation of a nucleotide occurs, hydrogen ions are released, effectively dropping the pH in the well. The ion sensing layer then detects the pH change as a rise in charge. If enough charge builds up, the sensor reads out this change in voltage built up across the sensing plate. In some embodiments, the sample may undergo PCR using any suitable method for performing PCR. Such methods may include, but are not limited to, the use of a thermal cycler or isothermal amplification, such as loop-mediated isothermal amplification (LAMP), nicking enzyme amplification reaction (NEAR), helicase-dependant amplification, recombinase polymerase amplification (RPA), or any other suitable method of performing a reaction including a detectable reaction byproduct. In some embodiments, thermal convection, such as microscale thermal convection or infrared-mediated temperature control may be used. In some embodiments, a heating element 220 may be fabricated into a substrate 202 as show in FIG. 2B. The heating element may be located in the substrate or under the sensing layer, or in any other suitable location on the device. In some embodiments, the heating element may be located in a cover or lid placed over the opening of the well which may serve to provide heat to the well and may or may not at least partially seal the well. In some embodiments, the heating element is an infrared heat source, such as for example, a tungsten lamp, radiation (the red part of the spectrum). In such an embodiment, cooling is achieved using heat dissipation or by compressed air.

In some embodiments, active heating/sensing elements may be integrated into a device or chip to perform independent PCR reactions (reactions which do not require the use of equipment outside of the device/chip). In some embodiments, conductor and semiconductor materials may be used to generate heat and/or other forms of electromagnetic radiation. In some embodiments, temperature sensing and heating may be accomplished through deposition of platinum, doped polysilicon, or any other suitable material. In some embodiments, an energy source may be coupled to a device. In some embodiments, the device may be coupled to a Peltier or other thermal source such as a thermal block, heat pad, or any other suitable heating source.

Fabrication of one or an array of wells in silicon with integrated actuators (heaters) for PCR monitoring has been described for example in U.S. Publication No. 20100301398 and Iordanov et al., *Sensorised Nanoliter Reactor Chamber for DNA Multiplication*, IEEE (2004) 229-232, both of which are incorporated by reference in their entirety. Wells or chambers thus fabricated might each be provided with an integrated ISFET for monitoring of nucleic acid amplification. As noted by Iordanov et al. in their above-noted paper, untreated silicon and standard silicon-related materials are inhibitors of Taq polymerase. Therefore, when silicon or a silicon-related material, e.g. silicon germanium or strained silicon (all such materials will hereinafter be referred to as a silicon substrate) is employed for fabrication of a microchip chamber or channel for nucleic acid amplification it will usually be covered with material to prevent reduction of polymerase efficiency by the silicon, such as, for example, SU8, polymethyl-methacrylate (PMMA), Perspex™ or glass.

Surface passivation of microfabricated silicon-glass chips for PCR is also described by Shoffner et al. in Nucleic Acid Res. (1996) 24, 375-379. In their studies, silicon chips were fabricated using standard photolithographic procedures and etched to a depth of 115 µm. PYREX™ glass covers were placed on top of each silicon chip and the silicon and glass were anodically bonded. Several types of surface passivations were investigated with a view to improving PCR amplification efficiency with thermo-cycling in the provided chamber. An oxidised silicon surface (SiO2) was found to give consistent amplifications comparable with reactions performed in a conventional PCR tube. Such a surface may also be favoured in fabricating a microfluidic device for carrying out nucleic acid amplification with ISFET pH sensing according to the invention. For further discussion of surface passivation in the fabrication of PCR microfluidic devices reference may be made to Zhang et al., *PCR microfluidic devices for DNA amplification*, Biotechnology Advances (2006) 24, 243-284. As described in that review article, as an alternative to static surface passivation by substrate coating, it may be possible to include a passivation agent in the sample (dynamic passivation).

As an alternative to low reaction volume chambers as described above for carrying out PCR monitoring in a stationary sample, the sample for PCR monitoring may be caused to flow through a channel or chamber of a microfluidic device and as it flows is subjected consecutively to different temperatures whereby thermo-cycling for PCR is achieved. Thus, for example, the sample may be caused to flow through a channel or chamber which passes consecutively through different temperature zones suitable for the PCR stages of denaturing, primer annealing and primer extension, e.g. a channel in a microfluidic device, such as, for example, a silicon chip device, which passes consecutively through zones of different temperature provided in the base suitable for successive repeats along the channel of the PCR stages of denaturing, primer annealing and primer extension. Such microfluidic structures for performing continuous flow nucleic acid amplification on a chip are described, for example, in Auroux et al., *Minaturised Nucleic Acid Analysis* Lab Chip (2004) 4, 534-546 and may be combined with ISFET monitoring of amplification. Structures of this type may be fabricated through the use of standard microfabrication techniques using for example photolithography to define the fluidic network and then an etching or deposition step to create the required channel or channels, for example in a PMMA, acrylic, PERSPEX™ or glass substrate. A cover plate in glass or PMMA or other material may or may not be overlaid to cover the channels. The base of the channel or channels may be formed by substrate bonding to a silicon chip with integrated ISFET and temperature sensors as well as heating or heat pump (Peltier) elements, such that the reaction mixture is in direct contact with these sensors and actuators, and may or may not include circuitry for temperature control. Alternatively, the base of the channel(s) may be formed by a printed circuit board (PCB) housing ISFET and temperature sensors such that these are in direct contact with the reaction mixture. The PCB may also house heating or heat pump elements, sensor interface and temperature control circuitry. Reagents present within the microfluidic channel or chamber may be those of the buffered amplification reaction mixture, which may include the primers chosen for ability to hybridize to the target at sites suitable for amplification of the chosen sequence, the required enzyme or enzmes for amplification and all four dNTPs in excess.

Temperature control may be achieved by a proportional-integral-derivative (PID) controller, which is one of the most common closed-loop feedback control systems. Errors between the measured temperature and the target temperature may be then used to calculate the level of heating required. Calculation of this output level may be performed based on the current error directly (proportional), the history of the error (integral), and the predicted future error based on its rate of change (derivative). Similarly, a PI controller may stabilize temperature based on present and historical values of the error as described in Iordanov et al. (2004) ibid. Alternatively, techniques such as pulse-width modulation or duty-cycling may be implemented.

It may alternatively be chosen to have a reciprocating system whereby the amplification mixture is moved backwards and forwards in a microchamber between the required temperature zones for thermo-cycling. It will be appreciated that nucleic acid amplification resulting from such on chip sample-shunting PCR (described in the above-noted review article of Auroux et al.) may be monitored by providing an ISFET in a wall of the microfluidic chamber, or in any suitable location for measuring pH.

For further details of microfluidic devices for PCR, which may be modified for ISFET sensing in accordance with the invention, reference may again be made to Zhang et al. (2006) Biotech. Adv. 24, 243-284. As discussed in that review article, while such devices may preferably take the form of silicon chips, other materials for the chip substrate may be employed such as glass, various polymers and ceramics. As an alternative to contact heating for thermo-cycling, various non-contact heating methods may be employed as also discussed in the same review article, including by way of example hot-air mediated heating, utilization of IR light, laser-mediated heating, induction heating and microwave irradiation.

Figure 3:
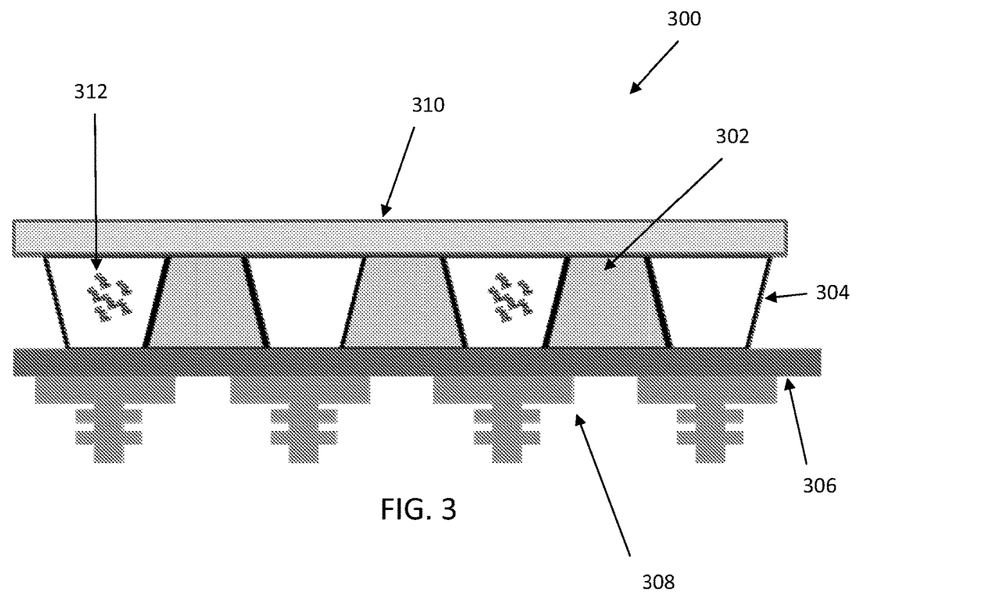
FIG. 3 shows one embodiment of the device for use with the method described herein.

In some embodiments, the device provided herein may be used to perform DPCR. FIG. 3 shows one embodiment of a device for use with DPCR. The device 300 may consist of a substrate 302 having a well 304, in some embodiments, at least 1 well, at least 100 wells, at least 1000 wells, at least 10,000 wells, at least 30,000 wells. In some embodiments, the substrate 302 may have less than 50,000 wells, less than 40,000 wells, less than 30,000 wells, less than 20,000 wells, less than 5,000 wells, less than 1000 wells, less than 500 wells, less than 100 wells, less than 10 wells. As shown in FIG. 3, the at least one well 304 may be located in chemical communication with a sensing layer 306 which may be in electrical communication with at least one sensor 308. In some embodiments, each well is in chemical and electrical communication with its own respective sensor 308. The sample 312, which may include, for example, the sample, PCR primers and reagents, buffers, or any other suitable reagent for amplification may be loaded on the chip. In some embodiments, a sealing layer 310, such as for example an immiscible fluid layer, a plastic layer, a glass layer, or any other suitable sealing layer, may then be positioned over the wells to isolate the reaction mixture in each of the individual wells. In some embodiments, at least a portion of the surface of the well may be coated with a hydrophilic coating or material. In some embodiments, at least a portion of the surface of the well may be coated with a hydrophobic coating or material. Additionally, the reaction mixture may then be subjected to conditions necessary for performing PCR. As previously described, as PCR occurs, hydrogen ions will be released each time the amplicon is extended/replicated thereby changing the pH of the reaction mixture in the well. This change in the pH of the reaction mixture may then be detected by the sensor in chemical communication with the well.

In some embodiments, the sample may be loaded onto the chip prior to amplification as previously described. In some embodiments, the sample may be amplified outside of the chip, or enriched, and then the sample with amplified template may be loaded onto the chip. Once on the chip, the sample may undergo any suitable reaction to release a detectable by-product. In some embodiments, small reaction volumes are formed by shearing a sample into smaller reaction volumes using an immiscible fluid, which are then loaded onto the chip.

Figure 4A:
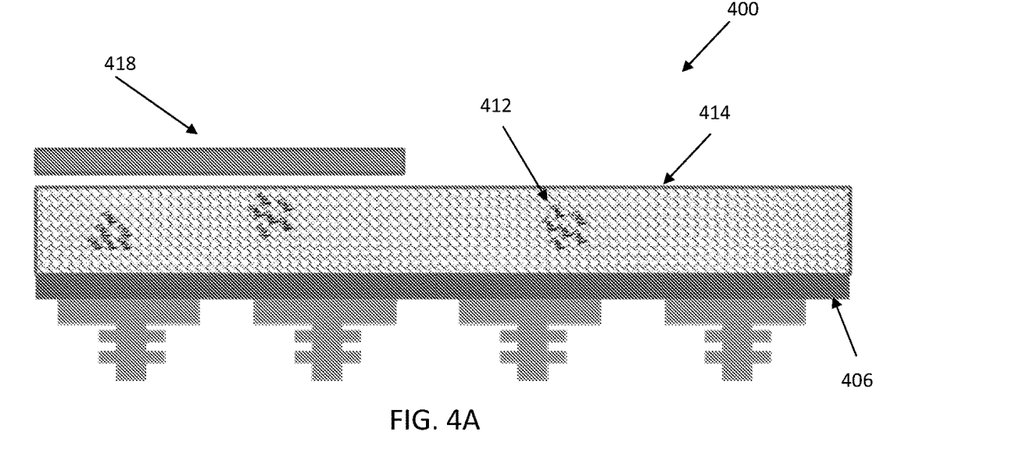
FIG. 4A & B show one embodiment of the device for use with the method described herein.
Figure 4B:
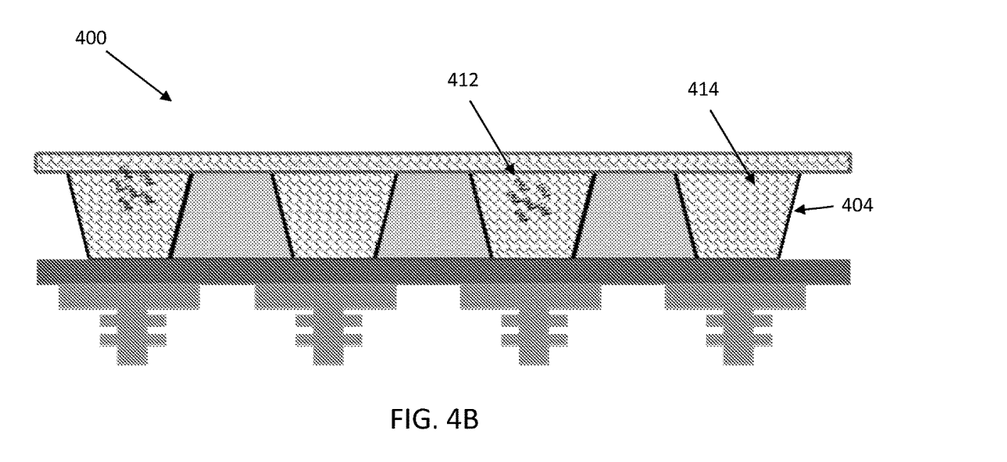

FIG. 4A shows an alternate embodiment of the device provided herein. As shown in FIG. 4A, in some embodiments of the device and methods provided herein, instead of dividing a sample among the wells in a substrate, a sample 412, such as DNA, may be contained and confined in a matrix 414 where individual molecules of DNA are isolated from each other. The matrix may be any suitable matrix including, but not limited to, an extracellular matrix, a polymer matrix, or gel, such as a polyacrylamide gel. The matrix should be of sufficient material to reduce the signal interference between DNA fragments, colonies, clusters, polonies. In some embodiments the matrix may be a continuous layer spread over the surface of the sensing layer 406, as shown in FIG. 4A. In some embodiments, the sample may be sandwiched between two glass slides and placed on the sensing plate. In some embodiments, a support 416 may be in structural communication with the matrix. In an alternate embodiment of the device 400, the matrix 412 may be used in conjunction with a substrate 402 containing at least one well 404, as shown in FIG. 4B. In such an embodiment, the wells 404 may be used to further reduce the signal noise between sample clusters and reducing the number of sensors detecting the signal from an individual cluster. The sensors below the individual colonies, clusters, polonies, fragments may then detect the change in pH for areas or wells with amplification each time an amplicon is extended and/or replicated as hydrogen molecules are released. The detection may depend on the proximity of the sample to a sensor or alternatively may be time based detection to identify the number of amplified polonies across the entire surface area. The quantification using the time based approach may then be done by calculating the number of colonies per area or volume.

Figure 5A:
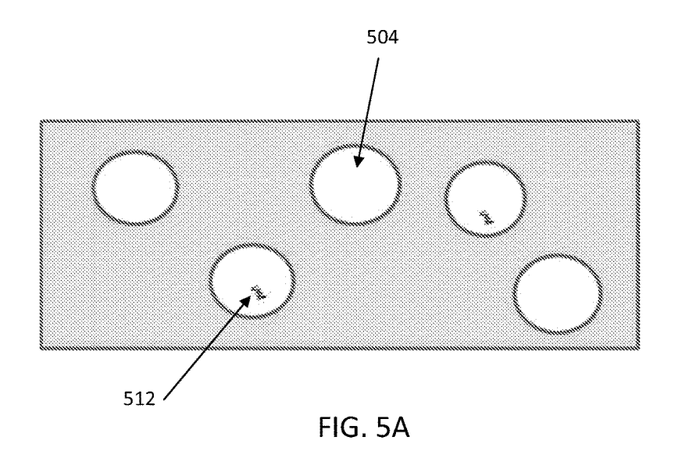
FIG. 5A & 5B show one embodiment of the device for use with the method described herein.
Figure 5B:
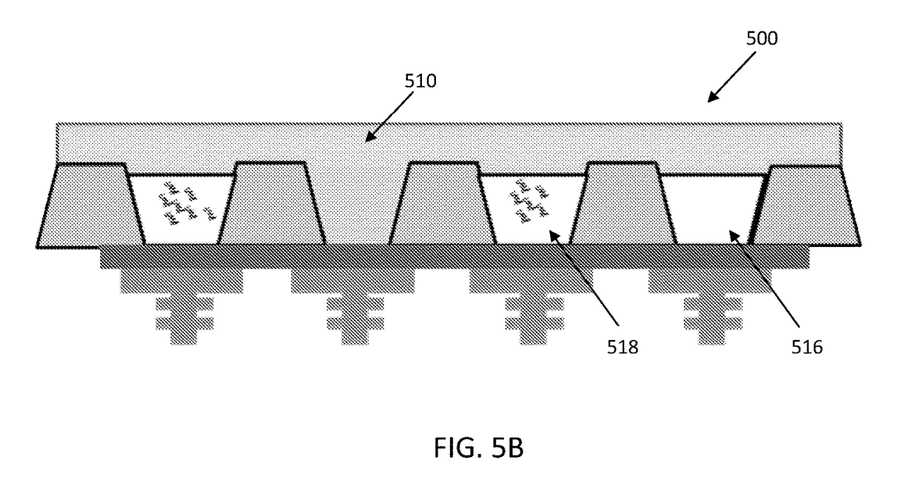
Figure 6A:
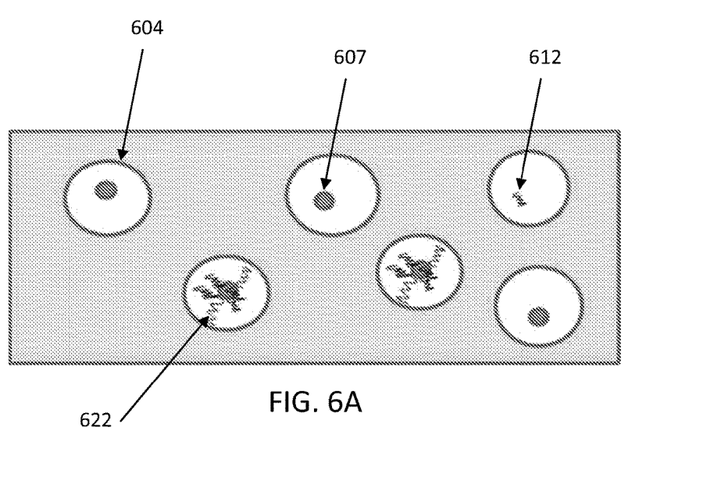
FIGS. 6A-6B show one embodiment of the device for use with the method described herein.
Figure 6B:
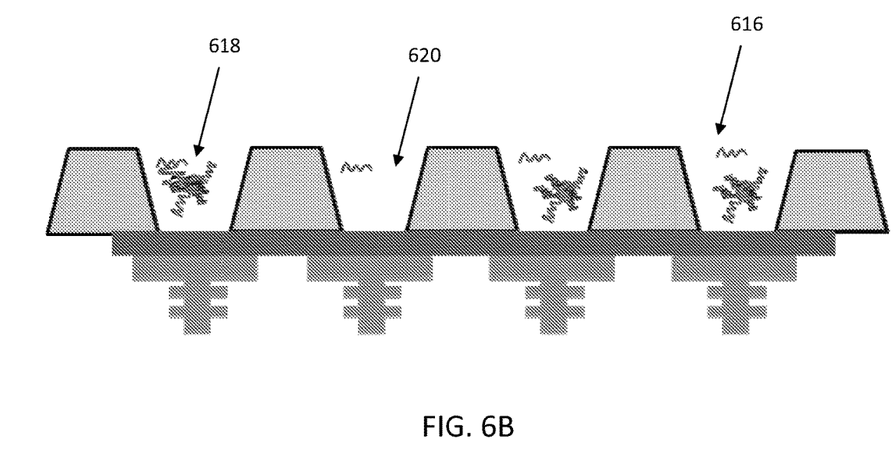

In some embodiments, the device may be used to perform emulsion dPCR. FIGS. 5A & 5B depict one embodiment of using the device with an emulsion. In such an embodiment, an emulsion may be created in which the emulsion droplets contain a sample of interest. In some embodiments, an emulsion may be created from a solution containing sample, primers, probes, reagents, buffers, or any other suitable component necessary for PCR. In some embodiments, a first emulsion may be created from a sample. A second emulsion containing reagents, probes, primers buffers, or any other suitable component for PCR, such as 5' nucleases or Taq-Man, may be created. In such an embodiment, the droplets from the sample emulsion and the droplets from the reagents emulsion may be coalesced at some point prior to amplification using any suitable form of energy including heat, light, current, chemical properties, charge, or any other suitable form for coalescing droplets. In some embodiments, the emulsion droplets may be formed using shaking, stirring, agitating, sonicating, or any other suitable method for forming an emulsion. In some embodiments, the unamplified emulsion droplets containing a sample 512 may be loaded onto a substrate 502 containing at least one well 504. FIG. 5A is a top view of a substrate showing samples 512 loaded into wells 504, wherein the sample 512 has been diluted down to contain a single copy of target nucleic acid. In such an embodiment, some of the wells may contain at least one template of a target nucleic acid and some of the well may contain zero templates of a target nucleic acid. In some embodiments, the surface of the wells may be treated with a surface coating, such as for example, a hydrophilic surface coating, a DNA binding agent or any other suitable treatment for retaining DNA molecules. Once the sample has been loaded on the substrate an immiscible fluid layer or a sealing layer 510 (as shown in FIG. 5B) may be placed over the wells to isolate the individual reaction volumes and may also act as an overlay. FIG. 5B shows the device 500 as seen from the side. In some embodiments, as shown in FIG. 5B, the sealing layer 510 may also fill any empty wells 504 which are not filled with sample. Once the samples have been loaded on the substrate 502, the sample may then be subjected to conditions necessary for PCR amplification. Wells containing amplified sample, or positive sample wells 516, may then be differentiated from wells with no target DNA, or negative sample wells 518. Additionally, non sample wells 520 may be distinguished from the positive sample wells 516 and the negative sample wells 518, since the non sample wells 520 will have different electrical properties due to the sealing layer In some embodiments, the device may be used with emulsion dPCR using beads, as shown in FIGS. 6A & 6B. In such an embodiment, an emulsion may be created which the emulsion droplets contain at least one template of a sample of interest and necessary PCR mixtures and/or reagents, probes, primers and a bead 607, wherein the bead 607 may include primer sites for binding DNA or any other target nucleic acid of interest. In some embodiments, the emulsion droplets may be formed using shaking, stirring, agitating, sonicating, or any other suitable method for forming an emulsion. Any beads 607 with DNA present will have DNA extended from the beads, or template positive beads 622. In some embodiments, enrichment of template positive beads may be done. The amplified emulsion droplets containing the sample 612 and the beads 607 may then be loaded onto a substrate 602 containing at least one well 604, as shown in FIG. 6A. In some embodiments, the surface of the wells may be treated with a surface coating, such as for example, a hydrophilic surface coating, a DNA binding agent or any other suitable treatment for retaining DNA molecules. In some embodiments, once the sample has been loaded on the substrate an immiscible fluid layer or a sealing layer may be placed over the wells to isolate the individual reaction volumes and may also act as an overlay. FIG. 6B shows the device 600 as seen from the side. Once the samples and/or beads have been loaded into the wells 604, the sample may then be subjected to conditions necessary for PCR amplification. In some embodiments, new primers and/or probes may be used to interrogate for an assay of interest. Wells containing beads, as opposed to empty wells 628, with the sequence corresponding to the assay of interest, or positive wells 624, will give a signal, otherwise the wells will be negative wells 628.

In some embodiments, an emulsion can be created with necessary reagents, primers, probes, and beads with primer sites. PCR may then be conducted on the emulsion so that beads with DNA present will have DNA extended from the beads to form template positive beads. The emulsion may then be broken. Positive beads may then be identified and enrichment of the positive beads may or may not be done. The beads may then be loaded onto chips which may or may not include wells. PCR may then be conducted on the chip and may be loaded with new primers to interrogate for an assay of interest. Wells with beads with the sequence corresponding to the assay of interest may then give a signal. Wells without beads corresponding to an assay of interest will then be negative.

In some embodiments of the method provided herein detection of hydrogen ions may occur without true sequencing. A non-sequencing hydrogen ion detection method may involve generating an amplicon with two target specific PCR primers, binding the amplicon to beads, hybridizing a target specific detection primer, loading the beads into the wells, doing bead detection on the chip to identify the wells with beads, supplying a reaction mixture with polymerase and all 4 dNTPs, and detecting hydrogen ions. In such a method the system may provide a count of how many beads have amplicons and match the detection primer, but would not necessarily provide any sequence information. The hydrogen ion spike would then indicate that polymerization of a DNA strand has occurred.

In some embodiments of the method detection of hydrogen ions may occur with partial sequencing of a target molecule, for example by identifying a sequence of the bead bound amplicon but which would not require a traditional 1:1 read out of the bases. In such an embodiment, a sequencing run may be performed using dNTP pools each of which was lacking of one of the four bases. This would give sequence patterns that could be used to positively identify a particular target molecule and which would also give more hydrogen ions per sequencing cycle and predictable variation in peak height.

Further provided herein is a method of performing ion detection without beads or wells. In such an embodiment, single amplicons would be bound to individual regions of hydrogel film located around the periphery of the hydrogen ion detector. A reaction may then be run to saturate the ring and then sequencing could be performed which would then release hydrogen ions to be detected by the hydrogen ion detector.

Provided herein is a method for performing digital castPCR, PAP, or TPAP extension assay. Competitive allele-specific TaqMan® PCR (castPCR) is a method of detecting and quantitating rare mutations in a sample that contains large amounts of normal, wild type genomic DNA (gDNA). castPCR™ technology combines allele-specific TaqMan® qPCR with allele-specific MGB blockers in order to suppress non-specific amplification from wild type alleles, resulting in better specificity than traditional allele-specific PCR, and is discussed further in copending application U.S. Ser. No. 13/350,764, Methods, Compositions, and Kits for Detecting Rare Cells, which application is incorporated by reference in its entirety. Phosphorylated activated polymerization (PAP) is a process involving pyrophosphorolysis-mediated primer-deblockings when hybridized with target or template nucleic acids followed by extension of the activated primers. The primers used in PAP typically include terminator nucleotides, such as dideoxynucleotides (ddNMPs) at 3'. TPAP refers to the polymerization of non-extensible prier in the presence of triphosphate. Usually, the non-extensible nucleotide at the 3' end of the primer is first removed to generate an extensible primer before the polymerization could occur. Digital castPCR, PAP, or TPAP extension assays may be also be used for rare mutation detection however detection sensitivities of thousands of hydrogens per well may be required. In such an embodiment, universal attachment of sheared gDNA (~100 kb each) including a rare mutant allele may be bound to a bead. During allele specific extension using castPCR or TPAP, as extension of the rare mutant allele occurs, hydrogen ions may be released. The released hydrogen ions may then be detected by an ion sensitive detection system.

In some embodiments, a nucleic acid may be amplified using activation by polyphosphorolysis (APP). APP may be carried out using the steps of: (a) annealing to a nucleic acid a first oligonucleotide which has a non-extendable 3' end ("P*") that is removable by polyphosphorolysis (i.e., activatable); (b) removing that 3' non-extendable terminus using a polyphosphorolyzing agent and a biocatalyst (i.e., a DNA polymerase) having polyphosphorolysis activity to produce an unblocked oligonucleotide; and, (c) extending the unblocked oligonucleotide to produce a desired nucleic acid strand. The APP method may also be used to amplify a desired nucleic acid strand by, for example, adding the following additional steps: (d) separating the desired nucleic acid strand of step (c) from the template strand, and (e) repeating steps (a)-(d) until a desired level of amplification of the desired nucleic acid strand is achieved. Steps (a) to (c) of APP can be conducted sequentially as two or more temperature stages on a thermocycler, or they can be conducted as one temperature stage on a thermocycler.

Further provided herein is a method for performing multiplex digital mutation detection assay using an ion sensitive detection system. In such an embodiment, allele specific primers may be attached to a bead. Each bead may be capable of analyzing 100-500 mutations. Multiplex emulsion TPAP PCR may then be performed in the presence of 0-1 molecules per bead. The beads and bound allele are then subjected to conditions for amplification. The presence or absence of mutations may then be counted and the frequency of these 100-500 rare mutations may then be determined. Other examples of TPAP or APP may be found in copending application U.S. Ser. No. 13/324,676, Polymerization of Nucleic Acids Using Activation by Polyphosphorolysis (APP) Reactions, which is incorporated by reference in its entirety.

Alternatively, a mixture of allele specific primers may be attached to beads. In some embodiments, at least 2 allele specific primers may be attached, at least 3 allele specific primers may be attached, at least 50, at least 100, at least 500, at least 1000. The beads may then be mixed with the sample and PCR reagents Further provided herein is a method for performing multiplex digital PCR using pre-amplification partitioning and dual-stage emulsion PC in a single step or single amplification reaction. Performing partitioning and amplification in a single step eliminates random noise or error and biases which may interfere with accurate quantification. In some embodiments, the partitioning of a sample, or the partitioning of a template molecule or nucleic acid occurs before any processing of the sample occurs. Processing may include for example, tailing, targeting, amplification, bead-loading, or any other suitable processing.

In some embodiments of the method of single amplification provided herein, the method may comprise partitioning a sample with a multiplex of targeting oligos which each contain a sequence specific 3' end and a universal 5' end, and wherein the targeting oligos are present in concentrations sufficient to ensure that several rounds of amplification of any target in the reaction volume may occur to produce a tailed amplicon of the target. Additionally, universal oligos may be added to the reaction volumes wherein the universal oligos are identical to the tails present on all targeting oligos, and wherein the universal oligos are present in sufficient concentration to continue amplification of any tailed amplicon beyond the first round. Furthermore, beads, such as sequencing bead for example, may or may not be present in the reaction volumes. In some embodiments, the reaction volumes may be monodisperse droplets, polydispersed droplets, and/or emulsions. In some embodiments, one step RT-PCR in emulsion may be possible and may allow for digital analysis of RNA.

EXAMPLES

Multiplex Digital PCR Using Pre-amplification Partitioning and Dual-Stage Emulsion PCR Materials: A multiplex pool of target specific oligos each tailed with the same universal sequence is combined in low concentrations with sample, and PCR MasterMix. For example: allele specific forward primers with desired number of targets, allele specific reverse primer with desired number of targets, universal forward primers or tail, universal reverse primer or tail, may be combined with the sample and PCR MasterMix. Additionally, beads preloaded with universal forward primers/tails may be added, as well as a higher concentration of matching universal forward primers or tails and matching universal reverse primers or tail. The amount of universal reverse primers or tails maybe in a slightly higher concentration than the universal forward primer or tail to drive bead loading.

Methods: Once the multiplex pool, sample, and PCR MasterMix have been combined, the reaction mixture may then be partitioned by emulsification into thousands or millions of droplets. Each droplet will therefore contain sufficient targeting primers to initiate amplification of every target. Amplification may then be started by whichever allele specific primers match the template in a particular droplet. All other allele specific primers are unproductive. After the first stage of amplification, the allele specific primers for the target may then be exhausted. Amplification may then be continued by the universal primers which are the same in every reaction or droplet. The universal forward primer on the bead may also be extended generating sequencing templates.

Analysis: Quantification of the droplet is digital (positive for amplification or negative for amplification).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby

What is claimed is:

1. A method of detection of a target nucleic acid comprising:
   providing a sample comprising an initial quantity of a target nucleic acid molecule;
   amplifying or enriching the sample to produce an amplified quantity of the target nucleic acid molecule;
   after amplifying, fractionating the sample into a plurality of sample volumes wherein more than 50% of the fractions contain no more than 1 of the target nucleic acid molecules;
   changing the ion concentration in one or more of the sample volumes by subjecting the plurality of sample volumes to conditions for amplification;
   detecting the change in ion concentration in the one or more of sample volumes; and
   determining the initial quantity of target nucleic acid in the sample.

2. The method of claim 1 further comprising combining a sample with primers and probes for amplification.

3. The method of claim 1 wherein the change in ion concentration is an increase in ion concentration.

4. The method of claim 1 further comprising combining a sample with a bead.

5. The method of claim 1 further comprising loading the sample on a substrate wherein the substrate includes at least one well.

6. The method of claim 5 further comprising sealing the at least one well with an immiscible fluid layer.

7. The method of claim 5 wherein the at least one well includes a coating.

8. The method of claim 7 wherein the coating is a hydrophilic coating.

9. The method of claim 1 further comprising positioning each of the plurality of samples in a plurality of isolated positions, wherein each of the plurality of isolated position is in chemical communication with a sensor.

10. The method of claim 1 wherein the change in ion concentration in an increase in hydrogen ions.

11. The method of claim 1 wherein the change in ion concentration is a change in pH.

12. The method of claim 1 further comprising quantifying the amount of a target nucleic acid.

13. A method for performing absolute quantification of a nucleic acid comprising:
   diluting a sample containing an initial amount of a target nucleic acid into a plurality of sample volumes wherein the percentage of reaction areas containing one or more target nucleic acid molecules is greater than 50% and less than 100%;
   changing a concentration of ions in two or more of the sample volumes by subjecting the plurality of sample volumes to at least one amplification cycle;
   detecting the change in ion concentration in the two or more of sample volumes after the at least one amplification cycle;
   quantitating an initial amount of target nucleic acid;
   wherein detecting comprises detecting both positive and negative ions.

14. The method of claim 1 where the change in ion concentration is an increase.

15. A method of detection of a target nucleic acid comprising:
   providing a sample comprising an initial quantity of a target nucleic acid molecule;
   fractionating the sample into a plurality of wells so that more than 50% of the wells contain no more than one of target nucleic acid molecules, wherein at least one of the wells contains at least one of the target nucleic acid molecule, at least one of the wells contain a portion of the sample with no target nucleic acid molecule, and at least one of the wells contains no sample and no target nucleic acid molecule;
   changing the ion concentration in one or more of the sample volumes by subjecting the plurality of sample volumes to conditions for amplification;
   detecting the change in ion concentration in the one or more of sample volumes;
   determining the initial quantity of the target nucleic acid in the sample; and
   detecting which well or wells contain no sample and no target nucleic acid molecule.

16. The method of claim 1 further comprising covering the sample volumes with a cover or lid, the cover or lid comprising a heating element configured to provide conditions for amplification.

17. The method of claim 1 wherein the sample volumes are contained in or on a sample holding device comprising a matrix, the matrix comprising a gel or a polymer forming a continuous layer over a surface of the sample holding device.

18. The method of claim 1 further comprising positioning each of the plurality of samples in a plurality of isolated positions, wherein:
   the plurality of isolated position are in chemical communication with a plurality of sensors; and
   two or more of the plurality of isolated position are in chemical communication with a single sensor of the plurality of sensors.

19. The method of claim 1 further comprising:
   prior to fractionating the sample, generating an amplicon with two target specific PCR primers;
   supplying the sample with polymerase and a plurality of dNTPs; and
   after fractionating the sample, detecting hydrogen ions.

20. The method of claim 19 wherein the plurality of dNTPs consist of only three different types of dPTPs.

* * * * *